(12) United States Patent
Huang et al.

(10) Patent No.: US 9,259,433 B2
(45) Date of Patent: Feb. 16, 2016

(54) SYNERGISTIC ANTIVIRAL COMPOSITIONS COMPRISING A VIRAL ATTACHMENT INHIBITOR, AN INTEGRATION INHIBITOR, AND A PROVIRAL TRANSCRIPTION INHIBITOR, AND THEIR USE

(71) Applicant: THE JOHNS HOPKINS UNIVERSITY, Baltimore, MD (US)

(72) Inventors: Ru Chih C. Huang, Baltimore, MD (US); Ibrahim S. Abd-Elazem, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 14/641,727

(22) Filed: Mar. 9, 2015

(65) Prior Publication Data

US 2015/0238511 A1     Aug. 27, 2015

Related U.S. Application Data

(62) Division of application No. 12/523,513, filed as application No. PCT/US2008/000530 on Jan. 16, 2008, now Pat. No. 9,005,889.

(60) Provisional application No. 60/880,388, filed on Jan. 16, 2007.

(51) Int. Cl.
| | | |
|---|---|---|
| A61K 45/06 | (2006.01) |
| A61K 31/704 | (2006.01) |
| A61K 31/216 | (2006.01) |
| A61K 31/343 | (2006.01) |

(52) U.S. Cl.
CPC ............ *A61K 31/704* (2013.01); *A61K 31/216* (2013.01); *A61K 31/343* (2013.01); *A61K 45/06* (2013.01)

(58) Field of Classification Search
CPC .. A61K 31/704; A61K 31/216; A61K 31/343
See application file for complete search history.

(56) References Cited

U.S. PATENT DOCUMENTS 9,005,889 B2 * 4/2015 Huang ................. A61K 31/704
424/208.1

* cited by examiner

*Primary Examiner* — Jeffrey Parkin
(74) *Attorney, Agent, or Firm* — Johns Hopkins Technology Transfer

(57) ABSTRACT

Compounds, compositions and methods for the treatment of HIV/HSP/HPV, in particular, compositions and methods for a 3 part combination therapy for HIV/HSV/HPV, comprising a viral attachment inhibitor, a viral sequence integration inhibitor, and a proviral transcription inhibitor. The therapy is advantageous for the treatment of HIV infection, and is also effective for HSV and HPV infection. Also disclosed are novel viral attachment inhibitors and methods of use.

5 Claims, 17 Drawing Sheets

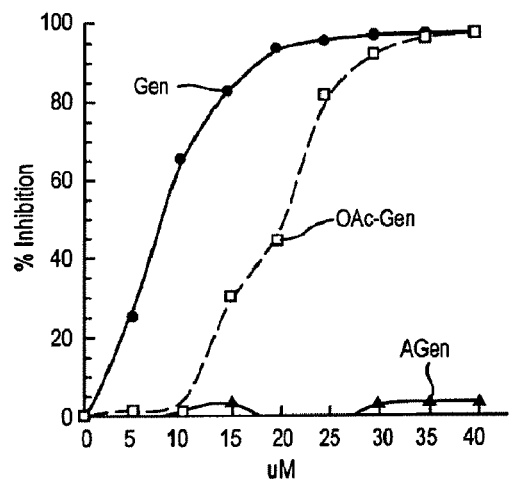
Fig. 6A
| Conc. | Acet. Gen. % Inhibition |
|---|---|
| 80 ug/ml | 95.5 |
| 40 ug/ml | 93.9 |
| 20 ug/ml | 91.5 |
| 10 ug/ml | 83.7 |
| 5 ug/ml | 0 |
| 2.5 ug/ml | 0 |
| 1.25 ug/ml | 0 |
Fig. 6B
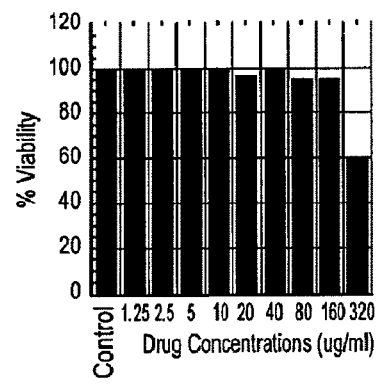
Fig. 6C

M₅22 (Lithospermic acid)
(4-[2-]1-carboxy-2-(3,4-dihydroxy-phenyl)-ethoxycarbonyl]-vinyl]-2-(3,4-dihydroxy-phenyl)-7-hydroxy-2,3-dihydro-benzofuran-3-carboxylic acid)

M₅32 (Lithospermic acid B)
(4-[2-]1-carboxy-2-(3,4-dihydroxy-phenyl)-ethoxycarbonyl]-vinyl]-2-(3,4-dihydroxy-phenyl)-7-hydroxy-2,3-dihydro-benzofuran-3-carboxylic acid 1-carboxy-2-(3,4-dihydroxy-phenyl)-ethyl ester)

TIEGHEMELIN
GEN-1

LITHOSPERMIC ACID
M₅22

TETRA-O-GLYCYL-NDGA
G₄N

SYNERGISTIC ANTIVIRAL COMPOSITIONS COMPRISING A VIRAL ATTACHMENT INHIBITOR, AN INTEGRATION INHIBITOR, AND A PROVIRAL TRANSCRIPTION INHIBITOR, AND THEIR USE

CROSS-REFERENCE TO RELATED APPLICATIONS

This application is a Divisional of U.S. patent application Ser. No. 12/523,513, filed Jan. 27, 2010, which is a 35 U.S.C. §371 U.S. national entry of International Application PCT/US2008/000530, having an international filing date of Jan. 16, 2008, which claims the benefit of U.S. Provisional Application No. 60/880,388, filed Jan. 16, 2007, the content of each of the aforementioned applications is herein incorporated by reference in their entirety.

The research resulting in the invention described herein was supported in part by Grant No. NIH 1RO1DE12165 from the National Institutes of Health. The U.S. Government has certain rights in the invention.

BACKGROUND

A recent WHO report has stated that there are 39.5 million people currently HIV positive worldwide. Of these, 4.3 million were infected in the year 2006 alone. AIDS deaths reached 2.9 million in 2006, which is the highest ever reported in any year. This number would have been even higher but for the recent progress made in providing the highly active antiretroviral therapy (HAART) to a large population of AIDS patients in underdeveloped countries. Nevertheless, there are still 40,000 new AIDS cases a year in the U.S. even with the HAART. Thus, alarmingly AIDS is on the rise worldwide (1).

Great effort has been focused on development of HIV-preventive vaccine during the past 20 years. However such vaccine research has met with unusual obstacles. As described in a recent article by Robert Gallo (2), it is not appropriate to develop HIV vaccines using attenuated live HIV because of the inherent danger of causing AIDS. Furthermore, there is no useful small animal model for studying HIV infection. The SIV/monkey model, while offering limited information on the mode of viral actions, is expensive in operation and generally not available to investigators. From many studies, we have also learned that the gp120 based HIV vaccine was not overly effective, and does not protect all strains of viruses containing highly variable regions of the $V_3$ loops. In addition, all recombinant HIV strains occur in vivo at an exceedingly fast rate.

The anti HIV compounds that are currently being used to treat AIDS patients include several reverse transcriptase inhibitors: zidovudine, didanosine, zalcitabine, stavadine, lamivudine and nevirapapine; and protease inhibitors: saquinavir, ritonavir, indinavir and others. It has recently been observed that these drugs, while very potent suppressers of wild type viruses, gradually lose their effectiveness with the appearance of a group of populated viral mutants.

Thus, the development of alternative therapeutic methods that inhibit HIV infection and protect host cell mediated immunity (CMI) is urgently needed.

BRIEF DESCRIPTION OF THE DRAWINGS

FIG. 6A-6C. Effect of Acetylated Gen.1 on HIV-1 and $CD_4^+$ Cells. 6A. Infectivity Assay by X-Gal Staining. 6B. Effect of Acetylated Gen.1 on Live HIV-1 replication and Infection. 6C. Effect of Acetylated Gen.1 on $CD_4^+$ Cell Viability FIG. 7 Inhibition of HIV-1 Replication by Non-Toxic Integrase Inhibitors $M_522$ and $M_532$ FIG. 8. Effect of $M_522$ and $M_532$ on Five Strains of HIV-1

DESCRIPTION

Figure 1A:
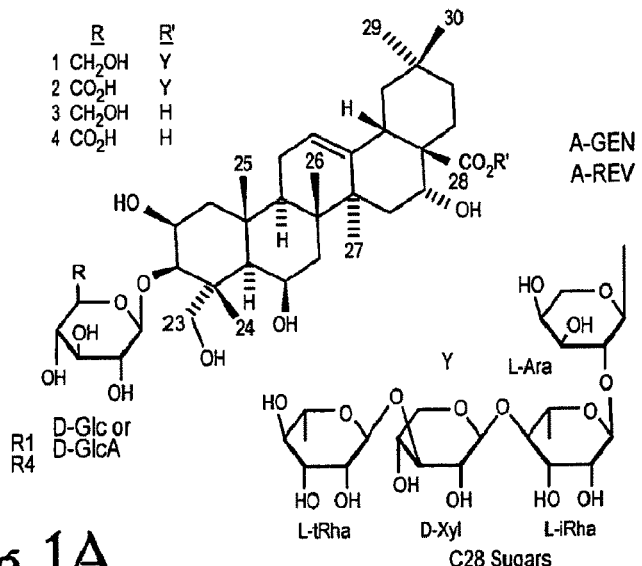
FIG. 1A. Structures of Rev.1, Gen 1, A-Rev and A-Gen

Described herein are compounds, compositions and methods for the treatment of HIV/HSP/HPV. In particular, disclosed are compositions and methods for a 3 part combination therapy for HIV/HSV/HPV, comprising a viral attachment inhibitor, a viral sequence integration inhibitor, and a proviral transcription inhibitor. The therapy is particularly advantageous for the treatment of HIV infection, and is also effective for HSV and HPV infection that is often present in HIV patients. Also disclosed are novel viral attachment inhibitors and methods of use.

Thus, the pharmaceutical compositions described herein for treatment of HIV infection, in the presence or absence of HSV and/or HPV infection include a viral attachment inhibitor, e.g. a triterpenoid saponin, such as arganine C (Rev. 1), Tieghemelin (Gen.1), or acetylated Tieghemelin, a viral sequence integration inhibitor, such as lithospermic acid ($M_522$) or lithospermic acid B ($M_532$), and a proviral transcription inhibitor, such as $G_4N$ or other nontoxic water-soluble derivative of NDGA with proviral transcription inhibitor properties. It has been found that this combination of drugs can block HIV-1 production in cultured $CD_4^+$ cells synergistically against a wide variety of HIV strains. The combination is equally active against mutant HIV strains that are highly resistant to currently available drugs against HIV protease and reverse transcriptase as compared to wild-type virus. Although the inventors are not bound by any particular theory, it is believed that the compositions and methods of the invention act by attacking the viral growth cycle at three different stages, i.e. by preventing HIV attachment to cell membranes, preventing viral sequence integration, and preventing proviral transcription. Effective amounts of the pharmaceutical components may be administered together in a single pharmaceutical composition, or separately, in two or three pharmaceutical compositions, either simultaneously, or at different times.

The pharmaceutical compositions described above can also be used in combination with other known antiviral and anti-HIV/HSV/HPV pharmaceuticals. For example, the compounds can be interchanged with other known HIV compounds and agents in the same classes (i.e. viral attachment inhibitors, viral sequence integration inhibitors, and proviral transcription inhibitors) to obtain the disclosed combination pharmaceutical, or other HIV therapeutic compounds and agents can be used to supplement the combination therapy. Examples of such FDA approved compounds and agents include entry and fusion inhibitors, such as Enfuvirtide (Fuzeon); non-nucleoside reverse transcriptase inhibitors, such as Delavirdine (Rescriptor), Efavirenz (Sustiva), Nevirapine (Viramune); nucleoside reverse transcriptase inhibitors, such as Abacavir (Ziagen), Abacavir/Lamivudine/Zidovudine (Trizivir), Abacavir/Lamivudine (Epzicom), Didanosine (Videx, Videx EC), Emtricitabine (Emtriva), Emtricitabine/Tenofovir (Truvada), Lamivudine (Epivir), Lamivudine/Zidovudine (Combivir), Stavudine (Zerit), Tenofovir disoproxil fumarate (Viread), Zalcitabine (Hivid), Zidovudine (Retrovir); protease inhibitors, such as Amprenavir (Agenerase), Atazanavir (Reyataz), Darunavir (Prezista), Fosamprenavir (Lexiva), Indinavir (Crixivan); Lopinavir/Ritonavir (Kaletra); Nelfinavir (Viracept); Ritonavir (Norvir), Saquinavir (Fortovase, Invirase) and ipranavir (Aptivus). Examples of current experimental compounds and agents for HIV treatment include entry and fusion inhibitors, such as AMD070, BMS-488043, Fozivudine tidoxil, GSK-873,140 (aplaviroc), PRO 140, PRO 542, Peptide T, SCH-D (vicriviroc), TNX-355, and UK-427,857 (maraviroc); integrase inhibitors, such as GS 9137, MK-0518, Microbicides, BMS-378806, C31G, Carbopol 974P (BufferGel), Carrageenan (Carraguard), Cellulose sulfate (Ushercell), Cyanovirin-N, Dextran sulfate, Hydroxyethyl cellulose, PRO 2000, SPL7013, Tenofovir, and UC-781; non-nucleoside reverse transcriptase inhibitors, such as Calanolide A, TMC125 (etravirine); and nucleoside reverse transcriptase inhibitors such as AVX754 (apricitabine), Alovudine, Amdoxovir, Elvucitabine, KP-1461, and Racivir.

Thus, the treatment methods encompass a method of treating HIV, HIV/HSV or HIV/HPV in humans comprising administering an effective amount of the pharmaceutical composition(s) described above to inhibit the growth cycle of HIV, and/or treat HIV symptoms in a person in need of treatment. Symptoms which may be alleviated by the pharmaceutical compounds and compositions include a low $CD_4^+$ count, sore throat, mouth sores, aching or stiff muscles, headache, diarrhea, swollen lymph glands, fever, fatigue, rash, including seborrheic dermatitis, frequent vaginal yeast infections.

Most, if not all, viral mutants, which include those explicatively active viral mutants, are host dependent in their replications. Host proteins, unlike viral proteins, when not under mutational pressure, are in general structurally invariable. Thus, compounds that block the usage of these cellular factors and membrane proteins at different stages of viral life cycle are likely to be good candidates as mutation-insensitive antiviral drugs. The work leading to the compositions and therapies described herein was initiated to specifically search for small chemical compounds that inhibit three cellular dependent steps of viral life cycle: to protect $CD_4^+$ cells against viral entry, to prevent chromatin dependent viral integration and proviral transcription of both wild type and mutant strains of HIV by changing the chromatin structure of HIV LTR which serves as promoter for such proviral transcription. This has resulted in a combinational drug design that protects host T lymphocytes against HIV with high efficacy and low drug resistance. Medicinal plants selected for have been based on three criteria: the crude materials of such plants must already be known as herbages which have been consumed by a large human population for thousands years, thus not likely to be overly toxic in long terms. Crude extracts must show significant antiviral activity at a concentration not damaging to the testing $CD_4^+$ cells and such plant materials should be available in large quantities suitable for pure compound isolations at low cost. Using this approach, we isolated and chemically modified a series of compounds which show specific antiHIV activities by preventing HIV attachment to $CD_4^+$ cells, by preventing HIV viral sequence integration, and by preventing HIV proviral transcription (3-6, 8-11, 15-23, 25). We have found these compounds (e.g. Gen-1, $M_522/M_532$ and $G_4N$ respectively), when tested in combination, can block HIV-1 production in culture $CD_4^+$ cells synergistically against a variety of HIV strains. They are equally active in targeting mutant strains that are highly resistant to currently available drugs against HIV protease and reverse transcriptase as compared to the wild type viruses. Furthermore, the combination is effective against other viral infections, such as HSV and HPV.

Viral attachment inhibitors are intended to include pharmaceutically acceptable compounds that inhibit the attachment of a virus (e.g. HIV, HSV, or HPV) to a cell surface.

Viral sequence integration inhibitors are intended to include any pharmaceutically acceptable compound that inhibits viral sequence integration in a human chromosome. Examples are lithospermic acid ($M_522$) and lithospermic acid B ($M_532$). These, and examples of other suitable compounds, are described in detail in U.S. Pat. No. 7,071,227 and more recently in Nunthaboot et al. European J. of Medicinal Chemistry, Article in Press 2006, available online @ www.sciencedirect.com.

Transcription inhibitors, for example $G_4N$, work by blocking transcription factor SP1 from binding to a variety of promoters of HIV, HSV and HPV genes. These drugs were found to be able to suppress the expression of viral growth related genes and growth of these three viruses (3). Isolation and chemical synthesis and modification of these plant-based compounds for antiviral testing in animals are the next logical step prior to engaging in phase I clinical trials for HIV, HIV/HSV or HIV/HPV infected patients (3, 4, 5, 10, 15, 21, 25).

The invention is to be understood as not being limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

All publications mentioned herein, including patents, patent applications, and journal articles are incorporated herein by reference in their entireties including the references cited therein, which are also incorporated herein by reference.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The compositions herein are formulated in accordance to the mode of potential administration. Thus, if the composition is intended to be administered intranasally or by inhalation, for example, the composition may be a converted to a powder or aerosol form, as conventional in the art, for such purposes. Other formulations, such as for oral or parenteral delivery, are also used as conventional in the art.

Compositions for administration herein may form solutions, suspensions, tablets, pills, capsules, sustained release formulations or powders.

DEFINITIONS

By "HIV" is meant Human Immunodeficiency Virus, including all strains of HIV-1 and HIV-2 that infect humans.

By "HSV" is meant Herpes Simplex Virus, including all strains of HIV-1 and HIV-2 that infect humans.

By "HPV" is meant all strains of Human papilloma virus.

"$G_4N$" means meso-1,4-bis[3,4-(dimethylaminoacetoxy)phenyl]-(2R,3S)dimethylbutane, either as a free base or preferably as a pharmaceutically acceptable salt, such as the hydrochloride salt.

"NDGA" means nordihydroguaiaretic acid. In addition to $G_4N$, suitable NDGA derivatives are described in U.S. Pat. Nos. 5,663,209, 6,214,874, 6,291,524, 6,365,787, 6,417,234, and 6,608,108.

By "derivative" is meant a compound with additions or substitutions, such as the addition of an acetyl group to a triterpenoid saponin, as disclosed herein. Other groups contemplated to be added are lower alkyl, acyl, alkoxy and the like ($C_{1-6}$). "Active derivatives" are those retaining the essential pharmaceutical properties of the parent compound (e.g. preventing HIV attachment to cell membranes, preventing viral sequence integration, or preventing proviral transcription). Derivatives may also consist of portions of the parent compound, wherein various substituents have been removed, or may consist of a particular substituent, if active (e.g. the substituent sugar, in the case of the triterpeoid saponins or by adding methyl groups to dihydroxyl-pheny rings in the case of $M_522$ and $M_532$ or by attaching one to four piperiino groups in the case of making water soluble NDGA derivatives $P_1N$, $P_2N$, $P_3N$ and $P_4N$).

Buffers suitable for use herein include any buffer conventional in the art, such as, for example, Tris, phosphate, imidazole, and bicarbonate.

As used herein, the terms "treatment," "treating," etc., refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or any adverse affect attributable to the condition or disease. "Treatment," thus, for example, covers: (a) preventing the condition or disease from occurring in an individual who is predisposed to the condition or disease but has not yet been diagnosed as having it; (b) inhibiting the condition or disease, such as, arresting its development; and (c) relieving, alleviating or ameliorating the condition or disease, such as, for example, causing regression of the condition or disease.

The term "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation. For example, the carrier for a formulation containing the present therapeutic compounds and compositions preferably does not include oxidizing agents and other compounds that are known to be deleterious to such. Suitable carriers include, but are not limited to, water, dextrose, glycerol, saline, ethanol, buffer, dimethyl sulfoxide, Cremaphor EL, and combinations thereof. The carrier may contain additional agents such as wetting or emulsifying agents, or pH buffering agents. Other materials such as anti-oxidants, humectants, viscosity stabilizers, and similar agents may be added as necessary.

Pharmaceutically acceptable salts herein include the acid addition salts (e.g. formed with a free amino group) and which are formed with inorganic acids, including, but not limited to hydrochloric or phosphoric acids, or such organic acids as acetic, mandelic, oxalic, and tartaric. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, and histidine.

The term "pharmaceutically acceptable excipient," includes vehicles, adjuvants, or diluents or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

As used herein, the singular forms "a", "an", and "the" include plural forms unless the context clearly dictates otherwise. Thus, for example, reference to "a compound" includes a plurality of such compounds.

Formulations, Dosages, and Routes of Administration

As mentioned above, effective amounts of the pharmaceutical compounds are administered to an individual, where "effective amount" means a dosage sufficient to produce a desired result. In some embodiments, the desired result is at least a stabilization or increase in CD4+ count in a patient.

Typically, the compositions of the instant invention will contain from less than about 1% up to about 99% of the active ingredient(s). The appropriate dose to be administered depends on the subject to be treated, such as the general health of the subject, the age of the subject, the state of the disease or condition, the weight of the subject, etc. Generally, between about 0.1 mg and about 500 mg or less may be administered to a child and between about 0.1 mg and about 5 grams or less may be administered to an adult. The pharmaceutical compounds can be administered in a single or, more typically, multiple doses. They may be formulated together into a single composition, or administered separately, either simultaneously or at different times. Preferred dosages for a given compound are readily determinable by those of skill in the art by a variety of means. Other effective dosages can be readily determined by one of ordinary skill in the art through routine trials establishing dose response curves. The amount of compound to be administered will, of course, vary depending upon the particular compound. Typical dosages of the therapeutic compounds are expected to be between 0.01 and 100 mg mg/kg/day, more preferably between 0.1 and 10 mg/kg/day, or between 0.1 and 1 mg/kg/day. It will be clear to those of skill in the art that for the combination pharmaceutical composition and method of treatment the dosage for each compound can be optimized, and equal amounts need not be administered.

The frequency of administration of the therapeutic compounds and compositions, as with the doses, will be determined by the medical practitioner based on age, weight, disease status, health status and patient responsiveness. Thus, the compounds/compositions may be administered one or more times daily, weekly, monthly or as appropriate as conventionally determined. The therapeutic compounds and compositions may be administered intermittently, such as for a period of days, weeks or months, then not again until some time has passed, such as 3 or 6 months, and then administered again for a period of days, weeks, or months.

The therapeutic compounds of the present invention can be incorporated into a variety of formulations for therapeutic administration. More particularly, the compounds can be formulated into pharmaceutical compositions by combination with appropriate, pharmaceutically acceptable carriers or diluents, and may be formulated into preparations in solid, semi-solid, liquid or gaseous forms, such as tablets, capsules, powders, aerosols, liposomes, nanoparticles, granules, ointments, solutions, suppositories, injections, inhalants and aerosols.

As such, although administration of the therapeutic compounds may be achieved in various ways, such as oral, buccal, rectal, intranasal, intravenous, intra-arterial, intra-tracheal, intraventricular, intracranial, interstitial, transdermal, etc., or by inhalation or implantation, most preferably, the therapeutic compounds are administered orally or intravenously.

In pharmaceutical dosage forms, the compounds may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the therapeutic compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the individual being treated.

The therapeutic compounds can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The therapeutic compounds can be utilized in aerosol formulation to be administered via inhalation, e.g. by formulation into pressurized acceptable propellants such as dichlorodifluoromethane, propane, nitrogen and the like.

Furthermore, the therapeutic compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the patient.

Kits with multiple or unit doses of the pharmaceutical compounds, are included in the present invention. Such kits, in addition to the containers containing the multiple or unit doses of the pharmaceutical compositions, optionally include an informational package insert with instructions describing the use and attendant benefits of the drugs in treating the diseases/conditions.

As will be evident to those of skill in the art, the compositions and methods described herein can also be used with pharmaceuticals used to treat opportunistic infections and the like which occur frequently in HIV patients.

This application claims priority to U.S. provisional application No. 60/880,388, filed Jan. 16, 2007, which is hereby incorporated herein by reference.

EXAMPLES

Example 1

Description of HIV Entry Inhibitors from *Tieghemella heckelii*: Optimization of a New Antiviral Saponin, the Acetylated *Tieghemella* (O Aceto-Gen-1) Against HIV-1 Viral Entry and Infection a. Isolation and Chemical Characterization of Two Antiviral Saponins from *Tieghemella heckelii*

*Tieghemella heckelii* (Sapotaceae, Th) is a large tree found in the West African rain forest. In January and February, the plant blossoms and develops ovoid fruits of 8 cm length and 7 cm diameter, which ripen in July-October. Many parts of the tree are used in traditional medicine. We have used a series of high-speed counter-current chromatography (HSCC), viral entry and infectivity assay and HIV-based cell-cell fusion assay to isolate specific HIV viral entry inhibitors from the ovoid fruits of the plants. The procedures for the isolation have been described in detail (4). Two pure saponin compounds, Arganine C (Rev 1) and *Tieghemella* (Gen. 1) have been isolated with the yield of 0.48% and 0.6% respectively. Rev.1 the more active of the two has an $IC_{50}$ of 2.8 μm while Gen-1 has an $IC_{50}$ of 17 μm (FIG. 1).

b. The C28 Side Chain Sugar of Rev-1 and Gen-1 is Essential for their Antiviral Activity.

In HIV infection, syncytia are the result of viral attachment and cell membrane fusion which create giant multi-nucleated cells consisting of both infected and uninfected cells. Rev. 1 and Gen. 1 have been shown to suppress syncytium formation resulting from co-culture of HeLa-$CD4^+$ cells and a CHO-WT cell line expressing wild type HIV-1 envelope (5). We found that arganine C (Rev-1) strongly inhibited HIV entry into CHO cells. *Tieghemella* (Gen-1) is less potent although less toxic than Rev-1. Rev-1 and Gen-1 are structurally identical except for one attached group at C23 (FIG. 1A). C23 glucose for Rev-1 and glucuronic acid for Gen-1 (4, 5). Their antiviral activity requires the C28 sugar chain. Removal of the four-sugar chains from Rev-1 and Gen-1 to give 16α-hydroxyprotobassic 3-0-β-D-glycopyransoide and 16α-hydroxyprotobassic acid 3-0-β-D-glucuronopyranoside respectively caused total loss of antiviral entry activity in both cases (A-REV and A-GEN). The four sugars in the substituent at the C28 position are L-arabinose, L-rhamnose, D-xylose and L-rhamnose (FIG. 1B).

c. Rev-1 and Gen-1 Target HIV-1 at the Viral Attachment Step to the HeLa $CD4^+$.

To determine whether the two saponins act exclusively at the attachment step, target HeLa $CD4^+$ cells were initially pre-cooled at 4° C. before viral exposure to exclude the possibility of virus internalization. Each compound, at graded concentrations, was then mixed with HIV particles and added to target cells in cold media. After a 30-minute attachment period, the cells were profusely washed to remove unbound virus. The amount of viral capsid in cell lysates was measured and a dose-dependent inhibition of attachment by Rev.1 and Gen.1 was observed (FIG. 2A). The two compounds exhibited somewhat variable activities at low concentrations (<10 μM) which became indistinguishable at the maximum concentration (20 μM). In contrast, when the side chain sugar of Gen-1 at C-28 was cleaved, the resultant sapogenin (Agen) was totally devoid of activity. Similar results were obtained in an HIV infectivity assay when target HeLa $CD4^+$ cells were challenged with virus particles and P24 antigen was monitored 48 hours later (FIG. 2B). No significant difference was found in the activity as also shown by the cell-cell fusion assay (FIG. 1). These inhibitory studies were repeated with infectious HIV virus tested under $P_3$ facilities. H9 cells ($4\times10^5$) were first incubated with compound and then infected with virus for one hour at 37° C. in $CO_2$ incubator to permit virus fusion and entry. The cells were then centrifuged and washed 3 times with phosphate buffered saline (PBS) to remove the unbound virus as described previously (6,7). The viral entry was determined by p24 antigen-capture assay. For the drug effect on HIV-1 replication and infection, the culture was incubated for 8 days. Viral replication was determined by the amount of HIV-1 p24 antigen in culture supernatant after 8 days of virus infection in H9 cells using the HIV/p24 monoclonal antibody assay (8). FIG. 3 describes the effect of Rev-1 and Gen-1 on viral replication and infection of the cells. Only low concentrations were used for testing to minimize the cellular toxicities of the drug.

d. Acetylation of C28 Sugars of Gen-1 Abolishes its Hemolytic Effect and Increases its Antiviral Activities without Cellular Toxicity.

We have found that Rev-1 and Gen-1 are antiviral saponins yet can cause damage to red blood cells at effective drug concentrations that blocked viral entry (FIG. 4). As such, Rev-1 and Gen-1 are both hemolytic, a property which may restrict potential use in therapy. To see whether modification of C28 sugar side chain can abolish such hemolytic effect, we acetylated the hydroxyl group of the C28 sugars with acetic anhydride. Briefly, 10 ml of pyridine and 5 ml acetic anhydride were added to a solution of pure *tieghemella* (Gen-1, 100 mg) in 5 ml methanol at 0° C. The solution mixture was allowed to reflux for five hours 0° C. The resultant mixture was extracted with water at 20° C. as described in reference 9. The aqueous solution was washed several times with dichloromethane. The water filtrate was dried under the hood to afford oAc-Gen-1; (160 mg). We compared the hemolytic effect of Gen-1 and oAc-Gen-1 by measuring the release of hemoglobin from red blood cells in the presence of Gen.1 or o-Ac Gen. The results demonstrated that modification of C28 sugars of Gen-1 by acetylation of the hydroxyl groups of the sugars can indeed eliminate the hemolytic effect of the Gen-1. As shown in FIG. 4, while o-Ac-Gen-1 showed no hemolysis at 57 μM, 50% of the red blood cells were lysed by Gen-1 at this concentration (9).

e. Acetylated Gen-1 is Able to Inhibit HIV-1 Replication with Minimal Effects on $CD4^+$ Cells.

A series of experiments demonstrated that the inhibitory effect of Gen 1 and acetyl Gen-1 on HIV attachment are similar, cells remained >95% viable above 90 μM yet inhibited HIV replication ($IC_{90}$) at about 10 μM (FIG. 5). Drug/virus Versus Drug/$CD4^+$ cells preincubation studies have further indicated that acetyl Gen-1 targets HIV virus instead of host cells. For example, preincubation of oAc-Gen-1 with $CD_4^+$ cells did not prevent HIV-1 entry and infection in $CD4^+$ cells while preincubation of oAc-Gen-1 with HIV-1 virus totally inactivated the infectivity of the testing HIV-1 (FIG. 5, 6, Ref 9).

Example 2

III. Isolation of Two Highly Potent and Non-Toxic Inhibitors of HIV-1 Integrase from *Salvia Miltiorrhiza* a. *Salvia* genus of Labiaceae family contains approximately 1000 species. 78 of these are distributed in different regions in China. *Salvia miltiorrhiza* root, commonly known as Dan-Shen root, has been used extensively for treatment of many diseases as antibacterial agent, for treatment of cardiovascular and cerebrovascular disease, against various types of hepatitis, chronic renal failure, etc. for centuries. Searches for chemical compounds which may be responsible for controlling these diseases has largely concentrated on using either lipophilic root extract or water soluble extract of the Dan-Shen roots. We found such a water soluble extract possesses exceptionally high antiviral activities against several types of viruses (HIV, SIV, HBS and MuLV) in infected cells and animals with extremely low acute toxicities (3). An $IN_i$ search was established based on an assay-guided purification procedure utilizing different concentrations of methanol, propanol, a two-layer extraction system (low salt water/butanol), and a high resolution inverted phase HPLC (Sperisorb OD S-2).

Figure 7:
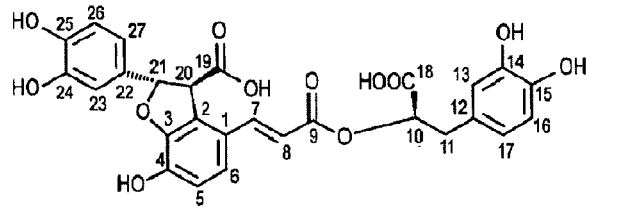
Figure 7:
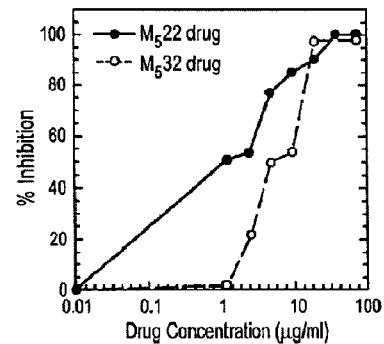
Figure 7:
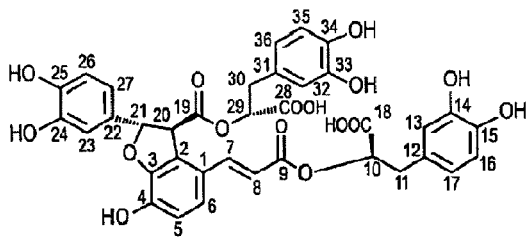
Figure 7:
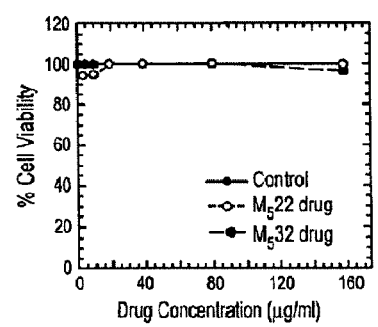
Figure 8:
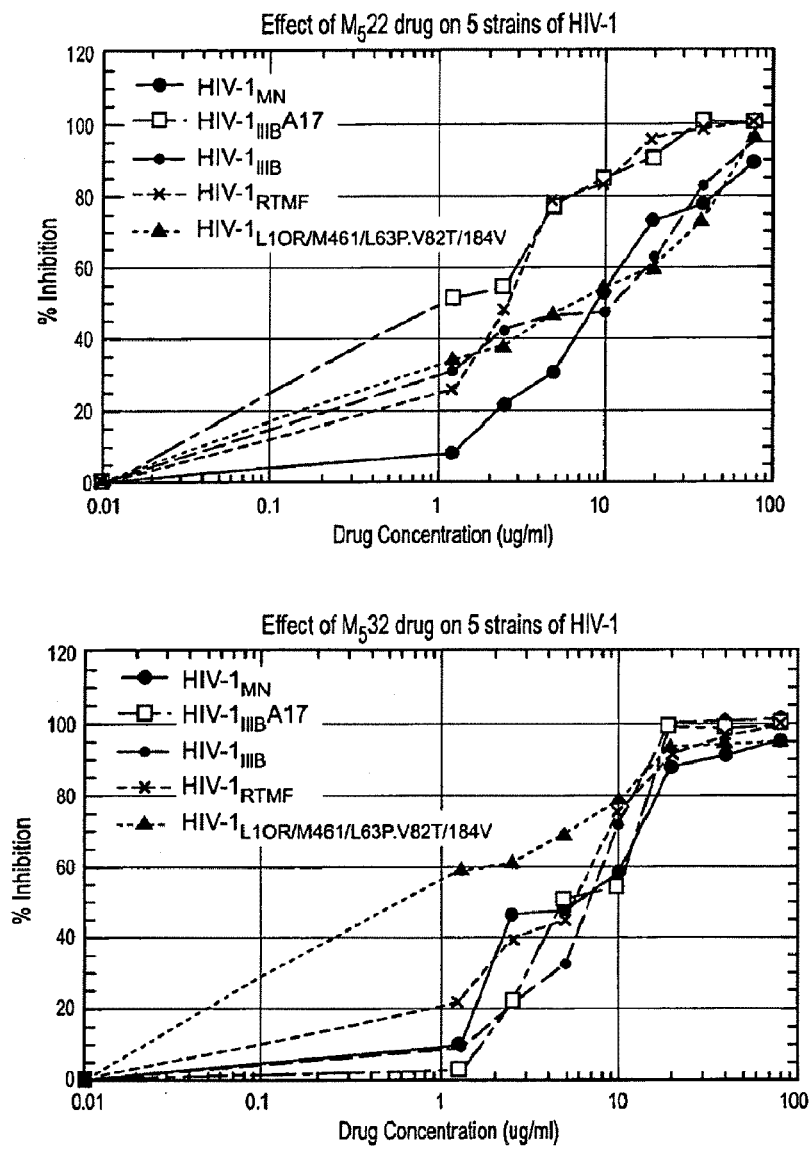

From SM roots, two compounds ($M_5 22$ and $M_5 32$) were isolated from *S. miltiorrhiza* roots in purities of >99.5% as shown by NMR special analysis with yields of 0.018 and 0.38%, respectively (10). Structural determination revealed that $M_5 22$ is lithospermic acid and $M_5 32$ is lithospermic acid B (FIG. 7). These two structurally related compounds are potent anti-HIV inhibitors and showed no cytotoxicity to H9 cells at high concentrations (CC100>297 µM for $M_5 22$ and >223 µM for $M_5 32$ (FIG. 7). In addition, $M_5 22$ and $M_5 32$ inhibited HIV-1 integrase catalytic activities of 3'-joining to the target DNA with an IC50 of 0.48 µM for $M_5 22$ and 0.37 µM for $M_5 32$ (11). Compound binding to HIV-1 integrase and inhibition of enzymatic activity within minutes. Neither $M_5 22$ nor $M_5 32$ by itself prevents HIV entry in H9 cells. They also show no inhibition of reverse transcriptase activity in infected cells (10,16). The levels of intracellular strong stop and full-length viral DNA remained unchanged following drug treatment. However, both inhibitors strongly suppressed the acute HIV-1 infection of H9 cells with IC50 values of 2 and 6.9 µM for $M_5 22$ and $M_5 32$, respectively. Thus these two selective integrase inhibitors should provide a novel class of therapeutic drugs for AIDS based on their high potencies and absence of cytotoxicity (10,11).

b. Inhibition of Acute Infection of Different Strains of HIV-1 by $M_5 22$ and $M_5 32$ The inhibitory effect of $M_5 22$ and $M_5 32$ against HIV replication was further examined using 5 different strains of HIV-1, drug resistant and primary isolates in the presence of a variety of drug concentrations in infected H9 cells. By using the HIV/p24 monoclonal antibody assay, the $IC_{50}$ (50% inhibitory concentration) for $M_5 22$ against HIV-1 drug resistant strain, HIV-1RTMF (AZT-resistant virus) was 2.5 µg/ml, 4.6 µM, HIV-1$_{IIIB}$A17 variant (highly resistant to inhibition by RT nonnucleoside inhibitors) was 1.1 µg/ml, 2 µM and for HIV-1$_{L1OR/M461/L63P.V82T/184V}$ (protease inhibitor resistant virus) the was 6 µg/ml, 11.1 µM. The HIV-1 primary isolate strains had $IC_{50}$'s of 11 µg/ml, 20.4 µM for HIV-1$_{IIIB}$ and 9 µg/ml, 16.7 µM for HIV-1$_{MN}$ (FIG. 8A). Similar results were obtained for the inhibition effect of $M_5 32$ against replication in these five different strains of HIV-1. $M_5 32$ inhibited HIV1$_{RTMF}$ (AZT-resistant virus) with an $IC_{50}$ of 6 µg/ml, 8.3 µM, HIV-1$_{IIIB}$A17 variant (highly resistant to inhibition by RT nonnucleoside inhibitors) with an $IC_{50}$ of 5 µg/ml, 6.9 µM and HIV-1$_{L1OR/M461/L63P/V82T/184V}$ (protease inhibitor resistant virus) with an IC50 of 1 µg/ml, 1.3 µM while it inhibited the HIV-1 primary isolate strains with an $IC_{50}$ of 7 µg/ml, 9.7 µM for HIV-1$_{IIIB}$ and of 6 µg/ml, 8.3 µM for HIV-1$_{MN}$ (FIG. 8B).

c. $M_5 22$ and $M_5 32$ Inhibit HIV Integration Step by Targeting Core Domain of (A.A.50-212) of HIV-1 Integrase.

Figure 9:
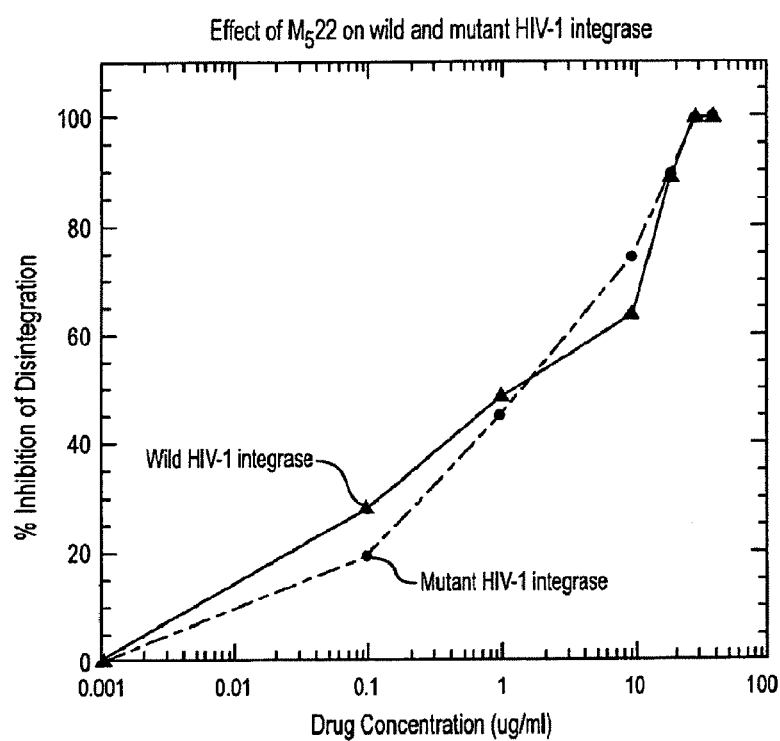
FIG. 9. $M_522$ Targets the Core Domain of HIV-1 Integrase
Figure 10:
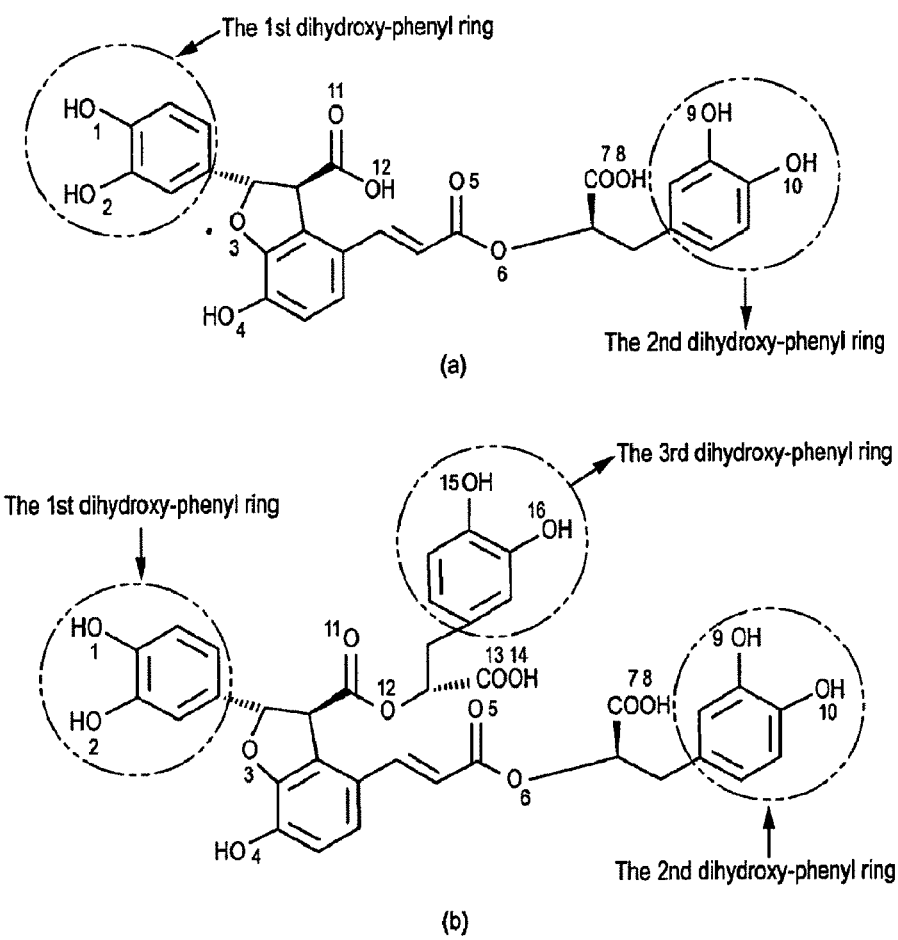
FIG. 10. Chemical structures of $M_522$ (a) and $M_532$ (b)
Figure 11C:
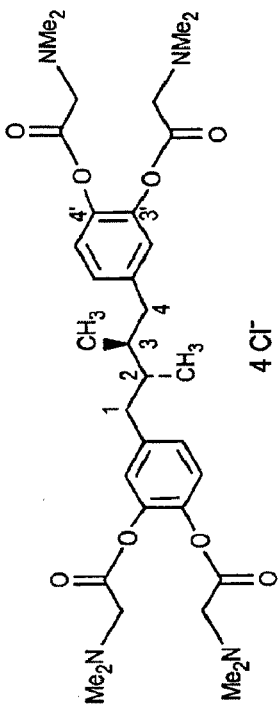
FIG. 11 A-D. Molecular Structures of Mal.4, $M_4N$, $G_4N$ and $P_4N$
Figure 11D:
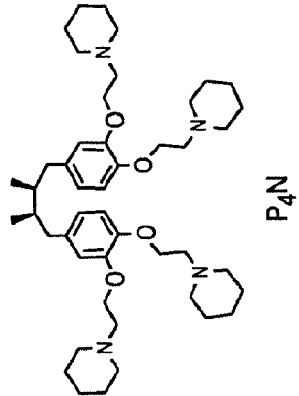
Figure 11A:
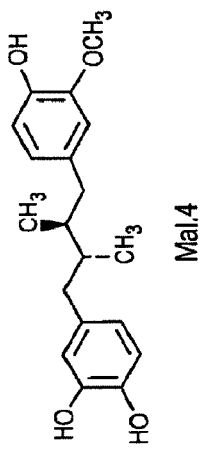
Figure 11B:
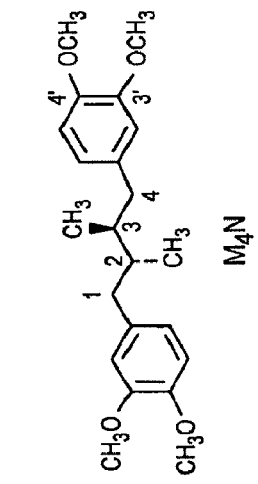

To determine whether $M_5 22$ and $M_5 32$ are acting against the catalytic core domain specifically, disintegration assay was tested using deletion mutant IN containing only the core domain of HIV integrase. Such deletion mutant is defective for normal integration, but it is capable of catalyzing a reversal of the forward reaction, termed "disintegration". The disintegration reaction can be assayed by using a deletion mutant HIV-1 integrase ($IN^{50-212}$) which lacks both the amino terminal zinc binding and the carboxyl terminal DNA binding domains but remains active in this assay, whereas such truncated IN loses activity in the 3'-processing and joining (strand transfer) assays. So, disintegration assay can be used to probe the site of drug-enzyme binding. As shown in FIG. 9, $M_5 22$ and $M_5 32$ inhibited both the wild type and the deletion mutant of HIV-1 integrase ($IN^{50-212}$) with equal efficacy which implies that integrase core domain contains the binding site of $M_5 22$ and $M_5 32$ and is responsible for the HIV-1 integrase inhibition (11).

d. $M_5 22$ and $M_5 32$ Protects Infected Cells from the Cytopathic Effects

A series of drug concentrations ranging from 1.25 µg/ml to 160 µg/ml were used for testing the cytotoxicity of $M_5 22$ and $M_5 32$ in H9 cells, using the MTT assay to determine the viability of H9 cells in culture. It was found that the cells remained viable during the entire culture period of 8 days even at the highest concentrations ($CC_{100}$) of $M_5 22$ and $M_5 32$ tested (160 µg/ml, 297 µM for $M_5 22$ and 160 µg/ml, 223 µM for $M_5 32$ Inhibition of HIV-1 replication by $M_5 22$ and $M_5 32$ was also examined in infected H9 cell cultures. H9 cells were infected with HIV-1$_{RTMF}$ (AZT-resistant virus) in the presence and absence of drugs. In the absence of drug syncytia are formed, while in the presence of drug, HIV-1 replication was inhibited in H9 cells and syncytia formation was prevented. Protection of the cells from the cytopathic effects was observed. In fact, the drug-protected, HIV-infected H9 cells appeared to be morphologically identical to the uninfected control cells (6).

e. Interaction of $M_5 22$ and $M_5 32$ with Amino Acids in the Catalytic Core Domain of HIV-1 Integrase as Determined by the Docking Calculations.

Although the binding modes of the two ligands are slightly different in some details, they shared some common binding sites (i) residues Glu92 and Lys 159 and (ii) the metal ion (11). Structural features of ligand that are crucial for the enzymatic activity are hydroxyl, aromatic ring, and carboxylic acid moieties. This could be supported by the docked conformations of both compounds $M_5 22$ and $M_5 32$ showing that ligand metal interaction, hydrogen bond interaction and hydrophobic attraction played a critical role in the binding between HIV-1 integrase and its inhibitors. This is described in more detail in reference 11.

Example 3

IV. NDGA Derivatives as Potent Mutation Insensitive Inhibitors for HSV, HPV and HIV Proviral Transcription a. NDGA Derivatives as Transcription Inhibitors for Suppressing HIV and HSV Viral Growth.

At least 33 different plant lignans (derivatives of Nordihydroguaiaretic acid, NDGA have been found to possess cytostatic activities (12). Several lignans of species podphyllum are also found to be effective in treating of venereal warts, influenza A, vaccinia viruses, herpes simplex type I and II (13). At high concentrations, NDGA inhibits several enzymatic activities. This harmful effect however can be greatly reduced when one of its catechol oxygens is blocked or when a hydrophobic group is added to the butane backbone in the mid-part of NDGA (14).

Figure 1B:
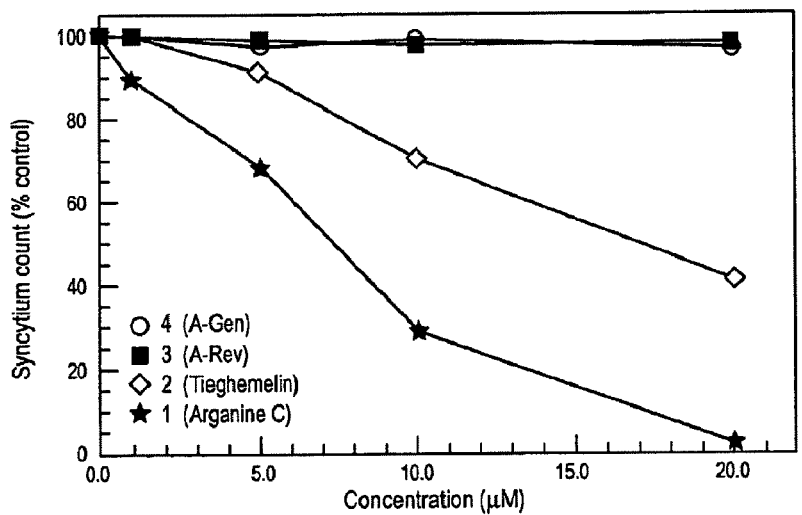
FIG. 1B. Antiviral Entry activity in HIV-based Cell-Cell Fusion Assay
Figure 2A:
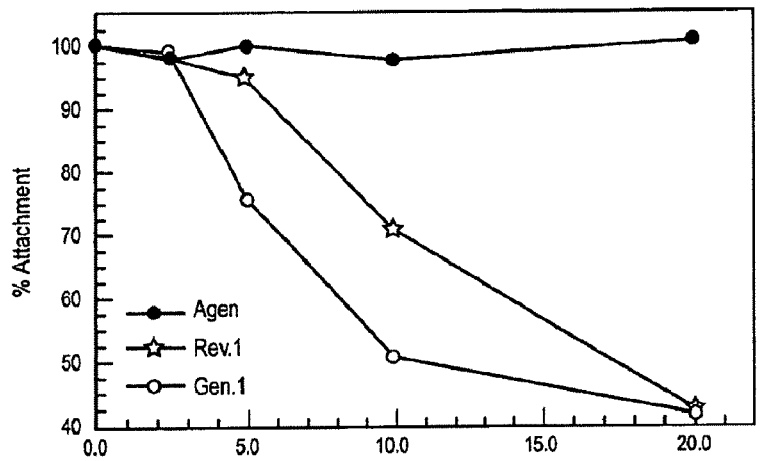
FIGS. 2A and 2B. Drug Effect on the Infectivity of HIV-1. 2A. HIV-1 Attachment. 2B. HIV Infection.
Figure 2B:
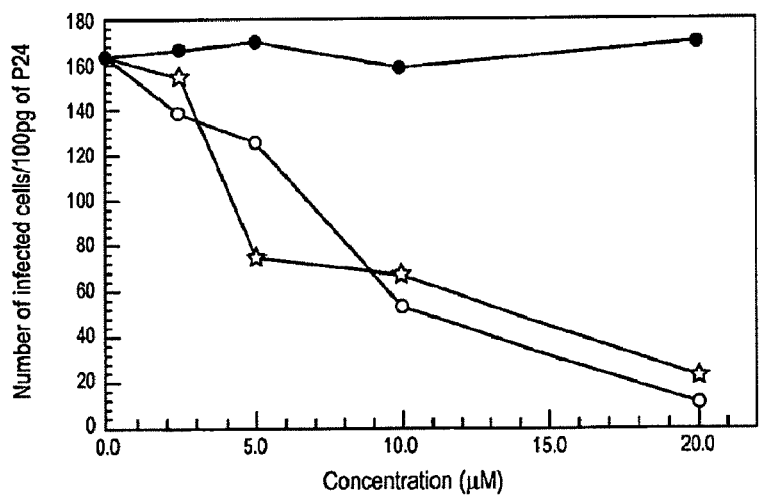
Figure 3:
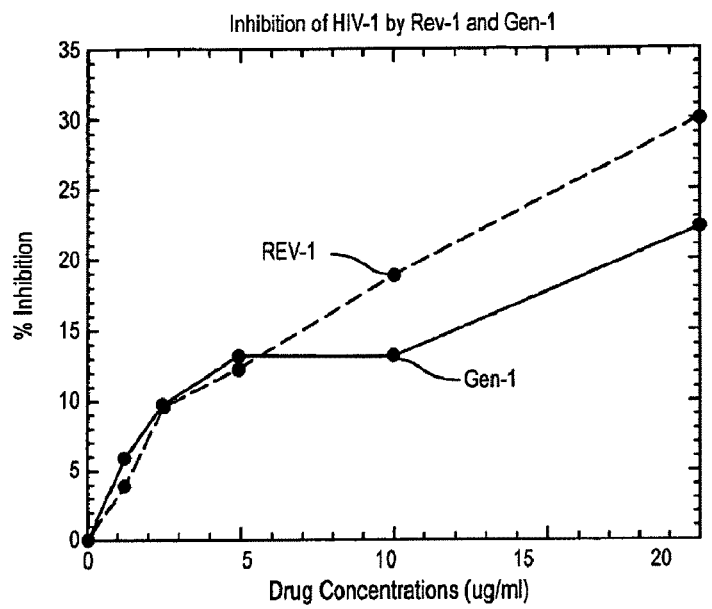
FIG. 3. Drug Effect on Replication of Infectious Live HIV-1
Figure 4:
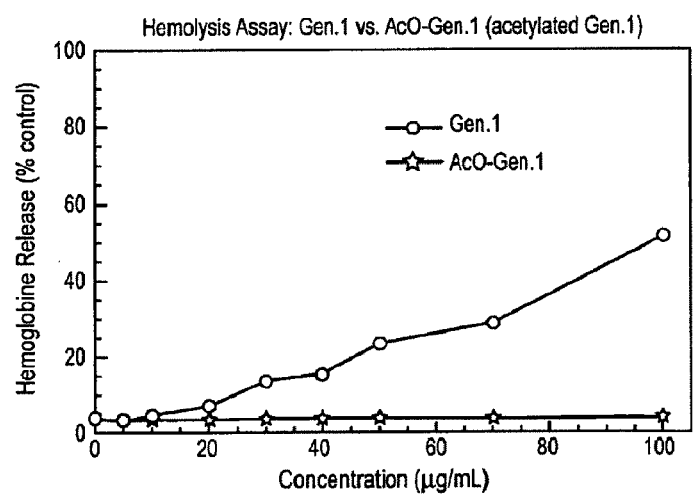
FIG. 4. Elimination of the Hemolytic Effect of Gen.1 by Acetylation of C28 Sugars FIG. 5. Inhibition of HIV-1 Replication and Maintained the Viability of the Treated Cells with Acetylated Gen 1
Figure 5:
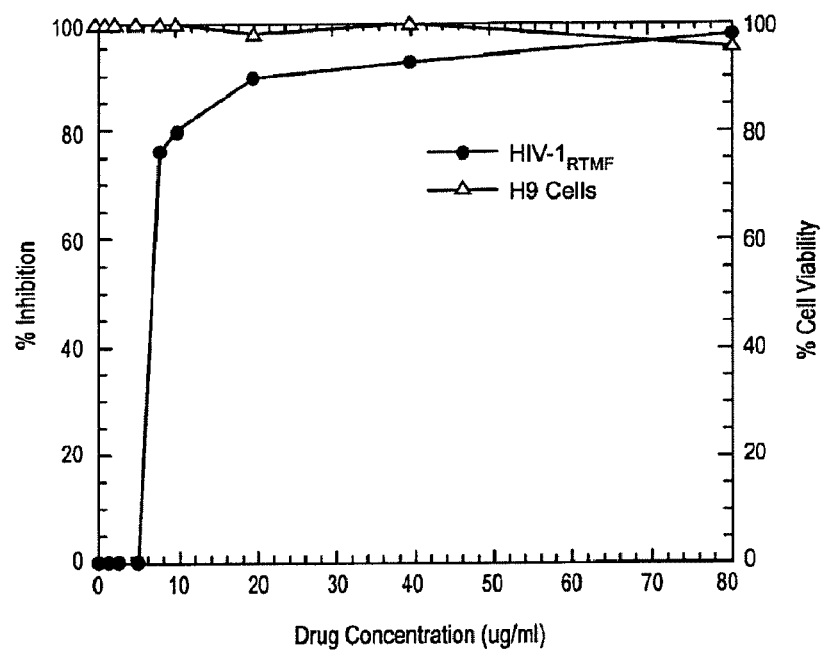

The mechanism underlying the antiviral action for NDGA derivatives was largely unknown before 1995. In 1995, Huang's group first reported a molecular study on 3'-O-methyl NDGA (FIG. 11, Mal 4)(15) isolated from creosote bush (*Larrea tridentate*) (16,3). We reported that 3'-O-methyl NDGA can specifically block HIV transcription, Tat-regulated transactivation, and HIV replication in human cell culture (3,15). NDGA derivatives interfere with the binding of transcription factor Sp1 to the promoter of the HIV proviral template. The target of Mal.4 is mapped to nucleotides −87 to −40, the Sp1 binding sites of the HIV long terminal repeat (LTR). Unmodified NDGA does not inhibit HIV transcription and has no effect on Sp1 binding in vitro. However, large preparations of such NDGA derivatives from plant sources are labor intensive and costly. In anticipation of the possible clinical use of lignans in controlling Sp1-regulated viral and tumor growth in humans, nine different methylated NDGAs and several water soluble NDGA derivatives were synthesized chemically in large quantities with low cost (17, 18, 26, FIG. 11). Unsubstituted NDGA was used as the parent substrate. $G_4N$ ("tetraglycinal NDGA", see FIG. 1, patent U.S. Pat. No. 6,417,234B1. Meso-1,4-BIS[3,4-(dimethylamino acetoxy)phenyl]-(2R,3S)-dimethyl butane hydrochloride salt was further used to conduct binding studies with HIV Sp1 enhancer sequence (3, 18, 19, 26, FIG. 11). NDGA derivatives bind to the major groove of the free DNA when it is uncomplexed with other proteins. The binding constant for $G_4N$/Sp1 enhancer sequence was calculated by the ethidium displacement technique at various phosphate buffer concentrations and pH values using a spectrofluorometer with excitation at 517 nm and emission at 596 nm. An apparent equilibrium binding constant ($K_{app}$) of $3 \times 10^6$ $M^{-1}$ was obtained by the equation $K_{app} = K_{EtBr}[EtBr]/[G_4N]$ which represents the concentration of the $G_4N$ causing a 50% reduction of the fluorescent intensity of DNA-ethidium solution (18). $P_4N$, another water soluble NDGA derivative with four attached piperidino group, has been found to disrupt Sp1 transcription factor binding to the major groove of Sp1 site either by competition for binding or by altering the overall DNA conformation such that the major groove becomes incompatible for Sp1 binding (FIG. 11) (19, 26). The inhibitory effect of a variety of NDGA derivatives against transcription of a variety of viral genes of HIV, HPV, HSV and several oncogenes have been described in U.S. Pat. Nos. 5,663,209, 6,214,874, 6,291,524, 6,365,787, 6,417,234, and 6,608,108 and references 3, 15, 16, 17, 20, 21A, 21B, 23, 25.

b. NDGA Derivatives are Potent Mutation-Insensitive Antiviral Agents Against HSV with High Clinical and Therapeutic Advantages.

Figure 12:
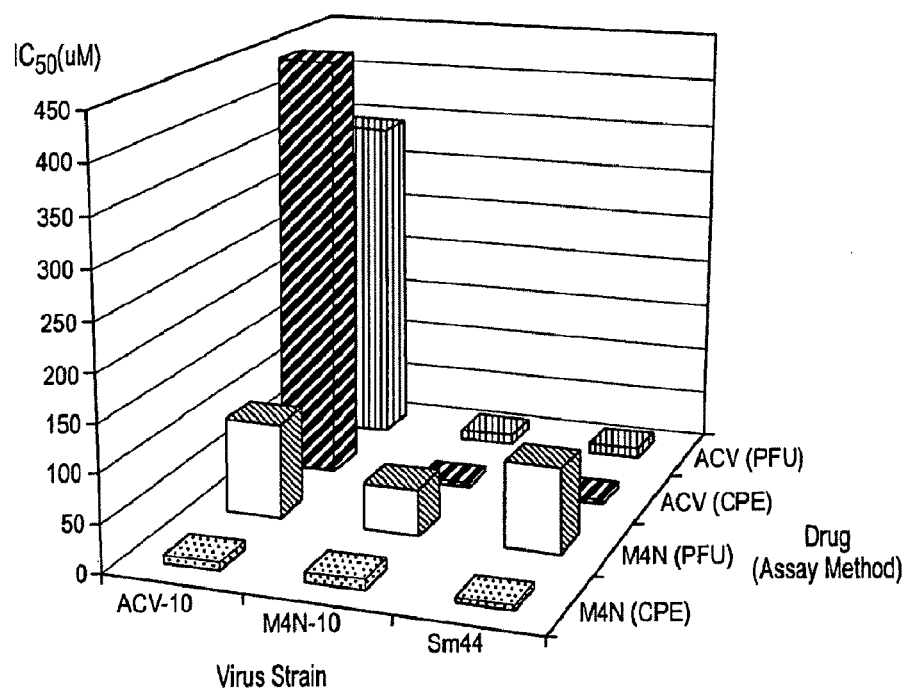
FIG. 12. Inhibition of Three Different Strains of HSV-1 in Vero Cells
Figure 13:
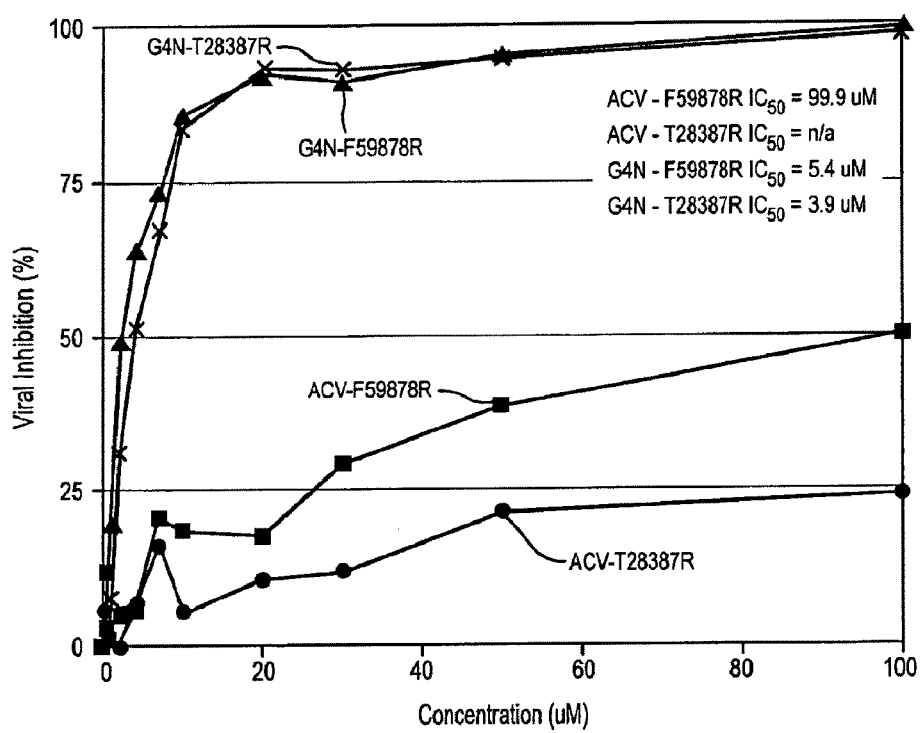
FIG. 13 Inhibition of Acyclovir-resistant Strains of HSV-1 by $G_4N$ and Acyclovir FIG. 14. Comparative Potency ($IC_{50}$) Between $M_4N$ and Acyclovir at Different HSV Passages of Drug Treatment FIG. 15. Efficacy of G4N and P4N Against HSV-2 in a Mouse Vaginal Model FIG. 16. Control of HIV Infection by Blocking Three Steps of the Life Cycle FIG. 17. The Three Compounds for Combination Therapy of HIV-1

The novel antiviral mode of action of NDGA derivatives confers several clinically relevant advantages which should significantly enhance their therapeutic value with regard to drug resistance, the prevention of HSV-1 reactivation, and as topically applied agents for the treatment of herpes labialis. Because the inhibitory mechanism of this class of compounds is completely distinct from the antiviral mechanism of nucleoside analogue agents, there is little possibility of cross-resistance between these two classes of drugs. We have demonstrated that $M_4N$ (FIG. 12) retains complete efficacy against acyclovir-resistant strains of HSV-1 (20), and the studies also showed that mutant acyclovir-resistant strains of HSV-1 (HSV-$1^R$) have no cross-resistance against $G_4N$ (FIG. 13) (21).

Figure 14:
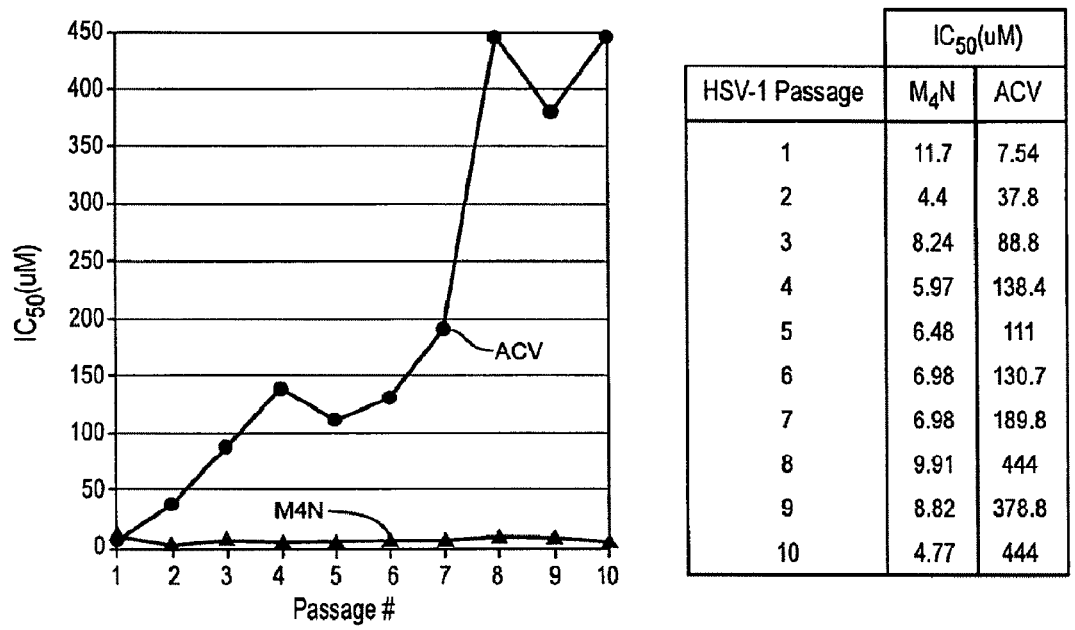

Another corollary to the mode of action of Mal.4, $M_4N$ and $G_4N$ is mutation-insensitivity. The capacity of harmful viral and bacterial strains in general, and of HSV-1 specifically, to mutate in response to conventional chemical agents poses a rapidly increasing problem in new drug design and the development of therapeutic strategies. Viral inhibitors such as nucleoside analogues which target viral factors have the advantages of high specificity and low cytoxicity. However in the clinical setting, prolonged use of these drugs places selective pressure upon the viral population to generate harmful resistant strains containing mutant proteins against which the drug is ineffective. Mutant acyclovir-resistant strains of HSV-1 have been commonly reported to contain altered TK and DNA polymerase enzymes (22), and repeated use of AZT and even the most effective reverse transcriptase (RT) and protease inhibitors leads to resistant HIV strains containing mutations found within HIV RT and protease enzymes. In contrast, host factors, unlike viral factors, are under no selective pressure to mutate and are in general structurally invariable. In comparative studies of mutation-insensitivity between $M_4N$ and acyclovir (20), there was no increase in the $IC_{50}$ of $M_4N$ against HSV-1 following ten passages of virus, indicating HSV-1 was incapable of developing resistance to $M_4N$ over the short-term. In contrast, the $IC_{50}$ of acyclovir increased from 7.54 µM in the first passage to 444 µM in the tenth passage of HSV-1 (FIG. 14, Ref. 21).

c. $M_4N$ and $G_4N$ as AntiHSV Agents in Animal Model Systems.

$M_4N$ and $G_4N$ were tested for their abilities to prevent HSV-1 infection in two animal model systems. The dorsal cutaneous guinea pig model system is a well-established model for HSV-1 infection that has been used in several studies to comparatively assess the potential efficacy of different topical formulations for treatment of herpes labialis. Straten M V, Carrasco D, Lee P, Tyring S K, Arch. Dermatol 137, 1232-1235 2001. Infected animals exhibited a dose-dependent response to treatment (measured by visual assessment): without $G_4N$, HSV-1 infection was obvious, at 5 µM $G_4N$, the drug was semi-effective and at 10 µM, it was more effective and at 150 µM $G_4N$ is extremely effective. $G_4N$ effectively inhibited HSV-1 induced cutaneous lesion formation and viral shedding, with no evidence of toxicity or dermal irritation even at the highest soluble concentrations (150 mM).

Figure 15:
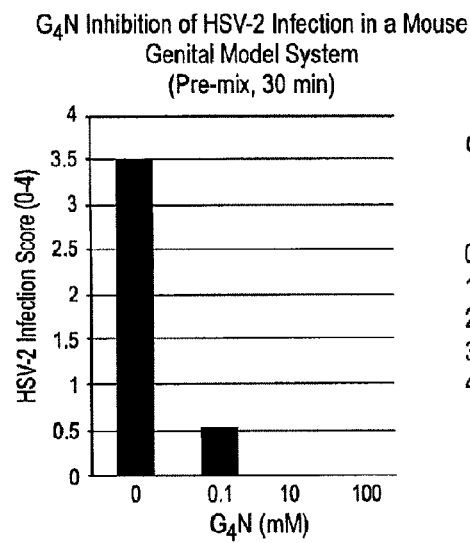
Figure 15:
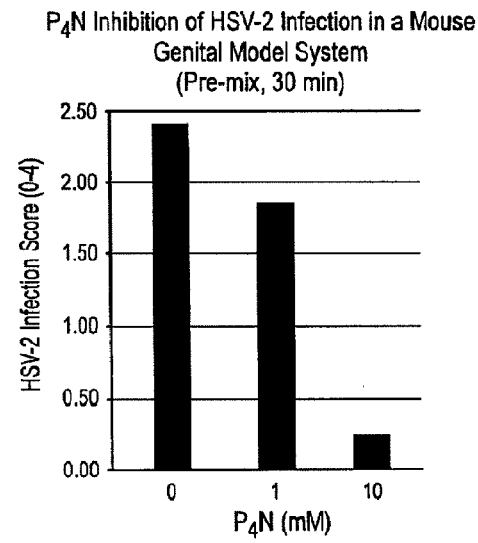

The efficacies of $M_4N$ and $G_4N$ against HSV-2 in a mouse vaginal model system were also examined. Progestin-treated female CF-1 mice (10 per group) were infected with HSV-2 in the absence or presence of $G_4N$ (in PBS), $P_4N$ (in PBS), or $M_4N$ in Vaseline (23). At the end of three days, the vaginal lavages were collected from the washings of the vagina regions. The status of the vaginal HSV-2 infection and replication were examined by their cytopathic effects on cultured human foreskin fibroblast cells. Monitoring and scoring were carried out by three persons independently. Data indicated that with no drug treatment, 9 out of 10 animals were infected with an average score of 3.5 (>75% infection) and with $G_4N$ at 0.1 mM only 1 out of 10 was infected with an average score of 0.5 (app 12.5% infection). There were no infections detected with $G_4N$ treatment at 10 mM or 100 mM. $P_4N$ was also found to be quite effective. At 10 mM concentration only 2 of 10 mice were weakly infected. An average scale of 0.19 was obtained (FIG. 15). For $M_4N$ treatment, because it was difficult to achieve total homogenous suspension of $M_4N$ with Vaseline, data were less impressive. Out of 8 mice, 4 were fully infected with a score of 3-4. However, the other 4 showed very little infection at a $M_4N$ concentration of 20 mg/ml. It is expected that better mixing of $M_4N$ in Vaseline at a higher concentration than 20 mg/ml (55.8 mM) should improve the efficacy of the treatment. All these compounds showed little toxicity in animals. For example, topical application for six days of $G_4N$ in guinea pigs at concentrations up to 50 mM showed no evidence of toxicity, and subdermal injection of $M_4N$ also showed no toxicity in mice.

Example 4

Combinational Therapeutics Targeting Laboratory and Clinical Isolates of HIV-1

Currently, there are 22 compounds representing four different mechanistic treatment classes that are used mostly in combination to treat HIV positive patients: nucleoside and nonnucleoside inhibitors for virus transcriptase (NRTi and NNRTi), viral protease inhibitors and viral fusion inhibitors. Combinational therapies using drugs from these different mechanistic classes were initially quite effective, which have resulted in overall decrease of HIV-1 morbidity and mortality in recent years. However, emergence of multidrug-resistant strains, and treatment related host toxicities became increasingly common with long time users of such drug treatment regimens. The discovery of host membrane protein CCR5 as coreceptor essential for CD4/gp120 interaction and viral-cellular fusion has led to the findings of CCR5 antagonists, MARA VIROC, Vicritrinoc, TAK-779 and the development of monoclonal antibody PRO140 against CCR5 recently. PRO140 binds as a competitive inhibitor for extracellular epitope on CCR5, while small molecular antagonists target hydrophobic pocket of CCR5. Antiviral synergy was reported between PRO140 and small-molecule CCR5 antagonists and with other classes of HIV inhibitors using HIV-1 pseudovirus assay, a self-inactivating vector from pNL4-3ΔENV-leuciferase vector (24).

Our combinational regimen is unique in several ways. (1) We have identified two HIV integrase inhibitors, $M_5 22$ and $M_5 32$, that are exceedingly active and non-toxic. (2) We have isolated a small molecular weight viral entry inhibitor (Gen-1) which uses its carbohydrate moiety to block HIV gp120 fusion, a mechanism different from others reported. (3) We have identified another mechanistic class inhibitor which blocks proviral transcription and post-integrations (for example, $G_4 N$, FIG. 11) and is equally active toward both wild type and drug resistant strains of HIV-1. This class of viral inhibitor targets viral transcription which uses all host cellular machinery that is not subject to selective pressure to mutate from drug treatment as shown for other viral protein inhibitors. We have demonstrated that when used in combination these compounds have a synergistic effect that permits the use of much lower dosages than would be otherwise necessary to achieve a therapeutic effect.

The efficacies of these drugs were tested individually and in combination against infection and replication of many strains of HIV-1 including the fresh clinical isolates from the infected patients.

Figure 16:
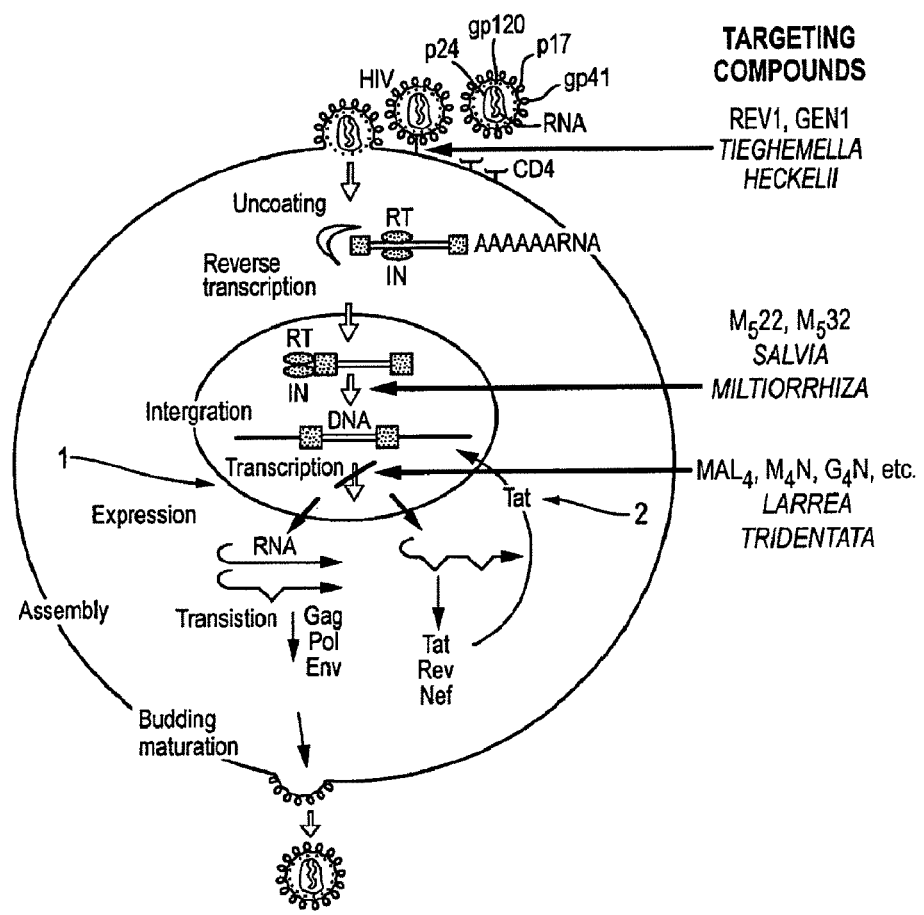

We tested drug combinations against two different cells infected with laboratory strain of HIV-1 RTMF. For these drug combinational studies, both the H9 cells and human PBMC have been used. We first tested how our inhibitors affect one specific strain of HIV which is resistant to drug against RT (HIV-$1_{RTMF}$). Briefly H9 ($1 \times 10^5$/ml) were infected with HIV-$1_{RTMF}$ strain with a multiplicity of infection of 0.1. These cells were further tested with three drugs, $M_5 22$, Gen-1 and $G_4 N$, either in combination or separately (8, 10, 21B). After 4-day incubation at 37° C., H9 cells were subcultured with fresh culture medium containing appropriate concentrations 0, 1.25, 2.5, 5, 10, 20, 40 and 80 μM of each of the drugs, or of a combination of all three of the drugs, each at the indicated concentration. The inhibition for HIV-1 by these combinations of drugs was examined using p24 assay after 8 days. It was found that $IC_{50}$ for the combination of the three drugs against HIV-1 is 1.3 μM (FIG. 16). In other words as combinational therapy, a $IC_{50}$ of 1.3 μM was achieved when 1.3 μM of each of these three drugs was used in combination.

Figure 17:
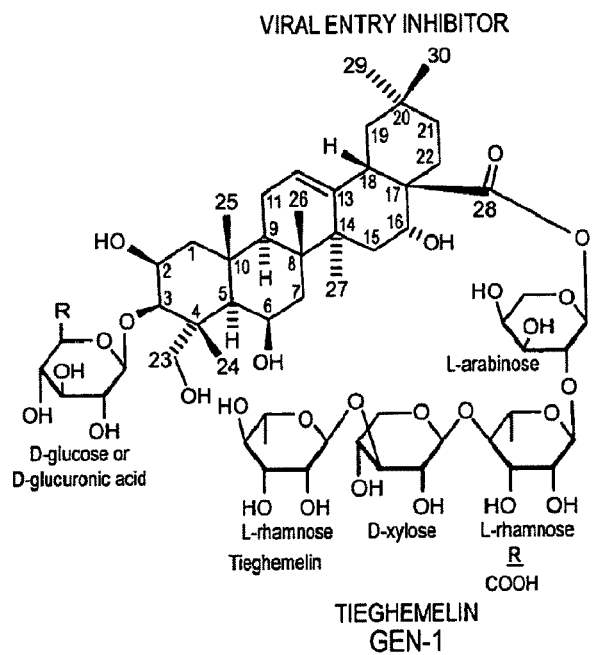
Figure 17:
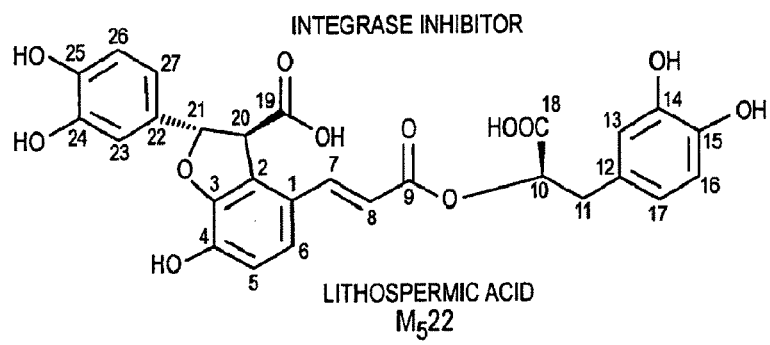
Figure 17:
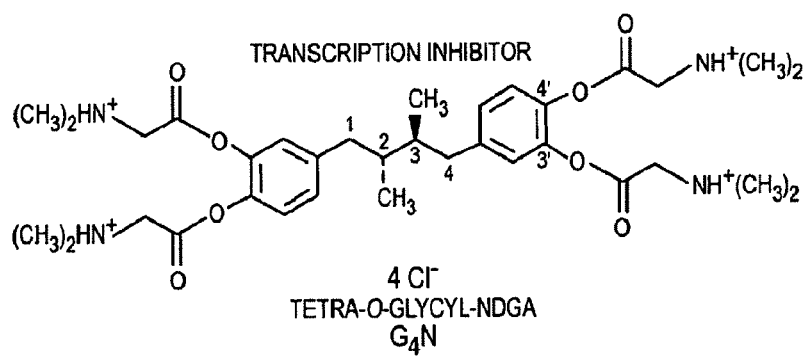
Figure 18:
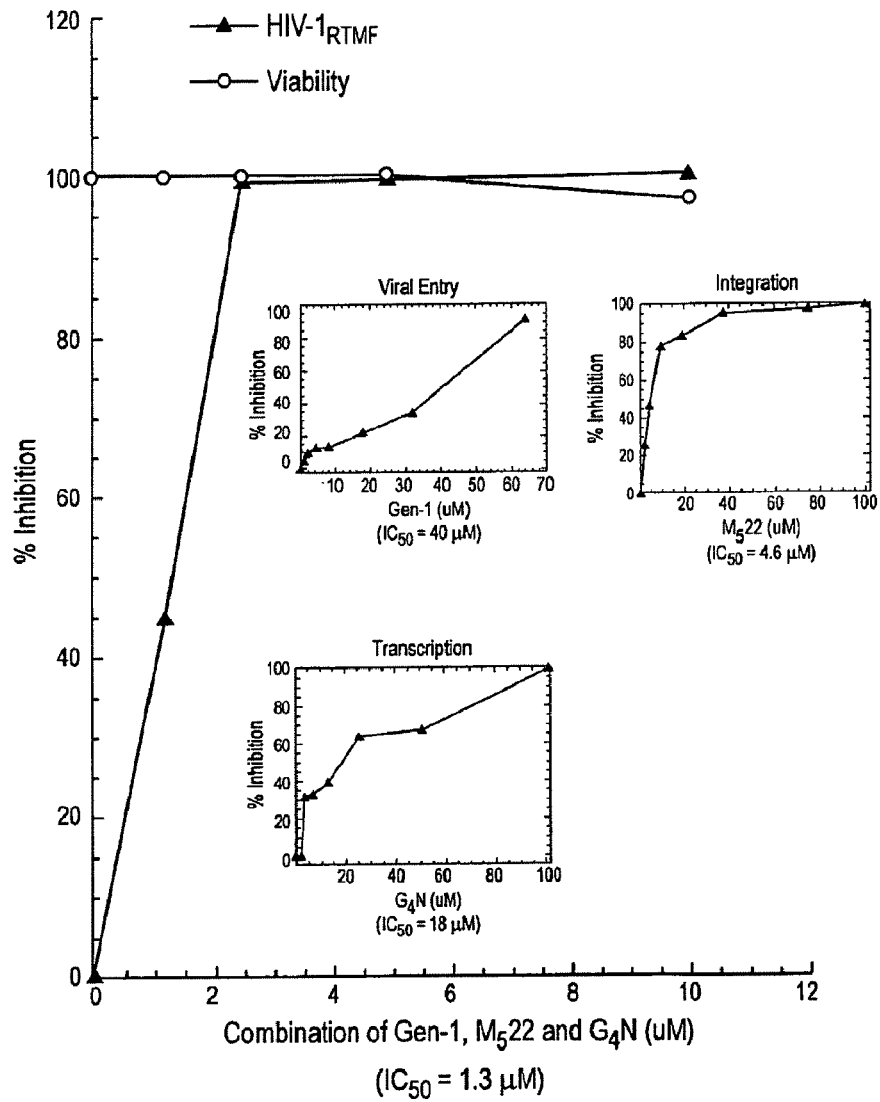
FIG. 18. Inhibition of HIV-1 Replication by Plant Compounds Either Alone or In Combination

Similarly, PBMC cells were isolated from a healthy blood sample and these cells were stimulated by PHA and IL-2. PBMC ($5 \times 10^6$/ml) were infected with HIV-$1_{RTMF}$. The cells were treated with three combinations of drugs, $M_5 22$, Gen-1 and $G_4 N$. Fresh media and drugs were added after 4 days with drug concentrations 0, 1.25, 2.5, 5, 10, 20, 40 and 80 μM. The inhibition for HIV-1 by these combinations of drugs was also examined by using p24 assay after 8 days. It was found that $IC_{50}$ for the combinations of three drugs against HIV-1 is 1.25 μM. On the other hand when tested alone with HIV-1 RTMF in H9 cells the $IC_{50}$ for Gen-1 (viral entry inhibitor), $M_5 22$ the integration inhibitor and $G_4 N$, proviral transcription inhibitor, are 40 μM, 4-6 μM and 18 μM respectively (See FIG. 16-18). In comparison, cytotoxicity for the three drugs combined to H9 cells was also analyzed using an MTT assay. As shown in FIG. 18, cellular toxicity to H9 cells combined was not detected in the presence of the three drugs, even when 12 μM of each was used.

In addition, the three drugs are being tested individually and in combination on PBMC cells infected with fresh clinical isolates of HIV-1 from AIDS patient. Blood samples were collected from a healthy donor, and PBMC cells were isolated by Ficoll-Hypaque density gradient centrifugation. These cells were stimulated by PHA and IL-2. PBMC cells ($5 \times 10^6$/ml), and infected with the clinical isolates of HIV-1 from an infected AIDS patient. These cells will be treated with the three drugs individually and in combination of M522, Gen-1 and G4N. Fresh media and drugs will be added every 4 days with drug concentrations 0, 1.25, 2.5, 5, 10, 20, 40 and 80 μM. The inhibition of HIV-1 by these drugs individually and in combinations will be tested by using p24 assay after 8 days similar to the protocol shown in FIG. 19. The results are expected to further confirm the advantages of the combination therapy.

References cited herein are listed below for convenience and are hereby incorporated by reference.

1. Altman L K "AIDS is on the rise worldwide, U.N. Finds New York Times, Nov. 22, 2006 www.UNAIDS
2. Gallo R C. The end or the beginning of the drive to an HIV-preventive vaccine: A view from over 20 years.
3. Huang R C C, Chang C C, Mold D. Survivin dependent and independent pathways and the induction of cancer cell death by tetra-O-methyl nordihydroguaiaretic acid. Editors D. Von Hoff and Gray P, Invited Article, *Seminars in Oncology* 33 (4), 479-485 (2006).
4. Gosse B K, Gnabre J N, Ito Y, Huang R C. Isolation of saponins with viral entry inhibitory activity by combined chromatographic methods. *J Liq Chromatogr Rel Technol.,* 25: 3197-3209 (2002).
5. Gosse B K, Gnabre J N, Bates R B, Nakkiew P, Huang R C C. Antiviral saponins from *Tieghemella heckelii. J Nat Products,* 65, 1942-1944 (2002).
6. Abd-Elazem I S. Isolation of two highly potent and non toxic inhibitors of human immunodefficiency virus type I (HIV-1) integrase and viral replication. JHU Ph.D. Thesis 2002.
7. Este J A, Cabrera C, Schols D, Cherepanov P, Gutierrez A, Witrouw M, Pannecouque C, Debyser C Z, Rando R F, Clotet B, Desmyter J, and DeClerco E. Human immunodeficiency virus glycoprotein gp120 as the primary target for antiviral action of AR177 (Vintevir). *Mol Pharmacol* 53, 340-345 (1998).
8. Gnabre J, Gosse B, Park R, Gallay P, Abd-Elazem I S and Huang R C. Triterpenoid saponins inhibit HSV-1 and HIV-1 infections by blocking viral entry. Manuscript in preparation.
9. Gosse B, Abd-Elazem I S and Huang R C. Acetylation of C28 sugars of GEN-1 abolishes antiviral activities without cellular toxicity. Manuscript in preparation.
10. Abd-Elazem I S, Chen H S, Bates R B, Huang R C C. Isolation of two highly potent and non-toxic inhibitors of human immunodeficiency virus type 1 (HIV-1) integrase from *Salvia miltiorrhiza. Antiviral Res.,* 55, 91-106 (2002).

11. Abd-Elazem I S, Nunthaboot N, Kokpol S, Painwanit S, and Huang R C. Inhibition of replication of drug resistant and primary isolates of HIV-1 by specific integrase inhibitors, $M_5 22$ and $M_5 32$. Manuscript in preparation for submission to *J Virol*.
12. Dewick P M and Jackson D E. Cytotoxic lignans from popodhylum and the nomenclature of aryltetralin lignans. *Pytochemistry* 20, 2277 (1981).
13. Bedows E and Hatfield G M. Studies on Podophyllotoxin, β-peltatin, Deoxypodophyllotoxin Picropodophyllotoxin and α-peltatin against Measles and Herpes Simplex Type I. *J. Nat Prod* 45, 725 (1978).
14. Schegg K M and Welch W. the effect of Nordihydroguaiaretic Acid and related lignans on Formyltetra Hydrofolate Synthesis and Carboxyl-Esterase. *Biochem Biophys ACTA* 788, 167 (1984).
15. Gnabre J N, Brady J N, Clanton D J, Ito Y, Dittmer J, Bates R B, and Huang R C. Inhibition of human immunodeficiency virus type I transcription and replication by DNA sequence-selective lignans. *Proc Natl Acad Sci USA* 92, 11239-11243 (1995).
16. Gnabre, J N, Bates, R B, Caldera, S and Huang, R C. Chemical Structure of HIV-Inhibitory Lignans from *Larrea tridentata*. *Tetrahedron*, 51, 12203-12210, 1995.
17. Hwu J R, Tseng W N, Gnabre J, Giza P, Huang R C. Antiviral activities of methylated nordihydroguaiaretic acids (I) Synthesis, structure identification and inhibition of Tat regulated HIV transactivation. *J Medicinal Chem.*, 41, 2994-3000 (1998).
18. King K Y, Hakimelahi G H, Huang R C and Hwa J R. Design, synthesis and binding studies of highly water soluble Nordihydroguaiaretic acid derivatives: a DNA major groove binder. *J of Gen and Mol Biol* 13 (No. 4), 248-257 (2002).
19. Dohm J A, Hsu M-H, Hwu J-R, Huang R C C, Moudrianakis E N, Lattman E E, Gittis A G. Influence of polyamines, ions, hydration, and the transcriptional inhibitor P4N on the conformations of the Sp1 binding site. *J Molec Bio* 349, 731-744, (2005).
20. Chen H, Li T, Li J N, Park R, Mold D, Gnabre J, Hwu J R, Tseng W N, Huang R C C. Antiviral activities of methylated nordihydroguaiaretic acids (II) Targeting herpes simplex virus replication by mutation insensitive transcription inhibitor tetra-O-methyl NDGA. *J Medicinal Chem.*, 41, 3001-3007 (1998).
21A. Park R, Giza P E, Mold D E, Huang R C C Inhibition of HSV-1 replication and reactivation by the mutation-insensitive transcription inhibitor tetra-O-glycyl-nordihydroguaiaretic acid. *Antiviral Res.*, 58, 35-45 (2003).
21B. Huang R C C, Li Y, Giza P E, Gnabre J N, Abd-Elazem I S, King K Y, Hwu J R. Novel antiviral agent tetraglycylated nordihydroguaiaretic acid hydrochloride as a host-dependent viral inhibitor. *Antiviral Res.*, 58, 57-64 (2003).
22. Hirsch M D, Kaplan J C, D'Aquila R I. Raven, Philadelphia. Antiviral Agents. In: Fields B N, Knipe D M, Howley P M, Chanock R M, Melnick J C, Monath T P, et al. (Eds.), Fields Virology, $3^{rd}$ ed pp. 431-466, 1996.
23. Park R, Mold D E and Huang R C. Direct virucidal effect of tetra-o-glycyl-nordihydroguaiaretic acid (G4N) on HSV-1 infection of vero cells and in a dorsal cutaneous guinea pig model system. Manuscript in preparation.
24. Murga J O, Franti M, Pevear P J, Maddon P J and Olson W C. Potent antiviral synergy between monoclonal antibody and small-molecule CCR5 inhibitors of human immunodeficiency virus type I. *Antimocrobial Agents and Chemotherapy* vol. 50, No. 10 p 3289-3296 (2006)
25. Craigo J, Callahan M, Huang R C, Delucia A L. Inhibition of human papilloma virus type 16 gene expression by nordihydroguaiaretic acid plant lignan derivatives. *Antiviral Res.*, 47, 19-28 (2000).
26. Hwu J R, Hsu M-H, Gitti R, Huang R C C. New nordihydroguaiaretic acid derivatives as anti-HIV agents. *J Med Chem*, Manuscript submitted.

We claim:
1. A method of treating HIV infection in an individual comprising the administration of effective amounts of a viral attachment inhibitor, a viral sequence integration inhibitor, and a proviral transcription inhibitor, in synergistic amounts, to an individual in need of treatment,
   wherein the triterpenoid saponin or derivative thereof is selected from the group consisting of arganine C (Rev. 1), Tieghemelin (Gen.1), acetylated arganine C or acetylated Tieghemelin,
   wherein the viral sequence integration inhibitor is lithospermic acid ($M_5 22$) or lithospermic acid B ($M_5 32$), and
   wherein the proviral transcription inhibitor is a nontoxic water-soluble derivative of NDGA selected from the group consisting of M4N, G4N, P4N and Mal.4.
2. The method of claim 1, wherein the proviral transcription inhibitor is GA.
3. The method of claim 1, wherein administration is oral.
4. The method of claim 1, wherein the effective amount is between 0.01 mg/kg/day and 100 mg/kg/day.
5. The method of claim 1, further comprising the administration to the individual of an effective amount of at least one or more anti-viral compounds selected from class of drugs consisting of non-nucleoside reverse transcriptase inhibitors, nucleoside reverse transcriptase inhibitors, and protease inhibitors.

* * * * *